United States Patent

Kristinsson et al.

[11] Patent Number: 6,136,039
[45] Date of Patent: Oct. 24, 2000

[54] DUAL DUROMETER SILICONE LINER FOR PROSTHESIS

[75] Inventors: Össur Kristinsson, Kópavogur; Hilmar Br. Janusson, Seltjarnarnes, both of Iceland

[73] Assignee: Ossur hf, Reykjavik, Iceland

[21] Appl. No.: 09/071,598

[22] Filed: May 4, 1998

Related U.S. Application Data

[60] Provisional application No. 60/045,704, May 6, 1997.

[51] Int. Cl.$^7$ ....................................................... A61F 2/78
[52] U.S. Cl. ................................................................. 623/36
[58] Field of Search ................................... 623/36, 37, 34, 623/32, 35, 33

[56] References Cited

U.S. PATENT DOCUMENTS

| | | |
|---|---|---|
| 980,457 | 1/1911 | Toles . |
| 2,696,011 | 12/1954 | Galdik . |
| 3,600,717 | 8/1971 | McKeehan . |
| 3,601,819 | 8/1971 | Herrmann . |
| 4,635,626 | 1/1987 | Lerman . |
| 4,923,474 | 5/1990 | Klasson et al. . |
| 5,376,129 | 12/1994 | Faulkner et al. . |
| 5,507,834 | 4/1996 | Leghi . |
| 5,603,122 | 2/1997 | Kania . |
| 5,728,168 | 3/1998 | Laghi et al. .............................. 623/36 |

FOREIGN PATENT DOCUMENTS 826041  12/1959  United Kingdom .

OTHER PUBLICATIONS

Silosheath brochure, Soft Socket Gel Liner, 4 pages, c. 1994.

*Primary Examiner*—David H. Willse
*Attorney, Agent, or Firm*—Bacon & Thomas, PLLC

[57] ABSTRACT

A silicone elastomer suspension liner for a prosthesis includes a soft inner silicone elastomer layer and a relatively harder outer silicone elastomer layer, with both layers being formulated to provide desired physical characteristics of the liner. An elasticity controlling matrix material and a prosthesis connecting element may be provided in the distal end area of the liner. The softer inner layer closely conforms to the residual limb that is to be fitted to a prosthesis while the harder outer layer provides durability and strength for the liner.

21 Claims, 1 Drawing Sheet

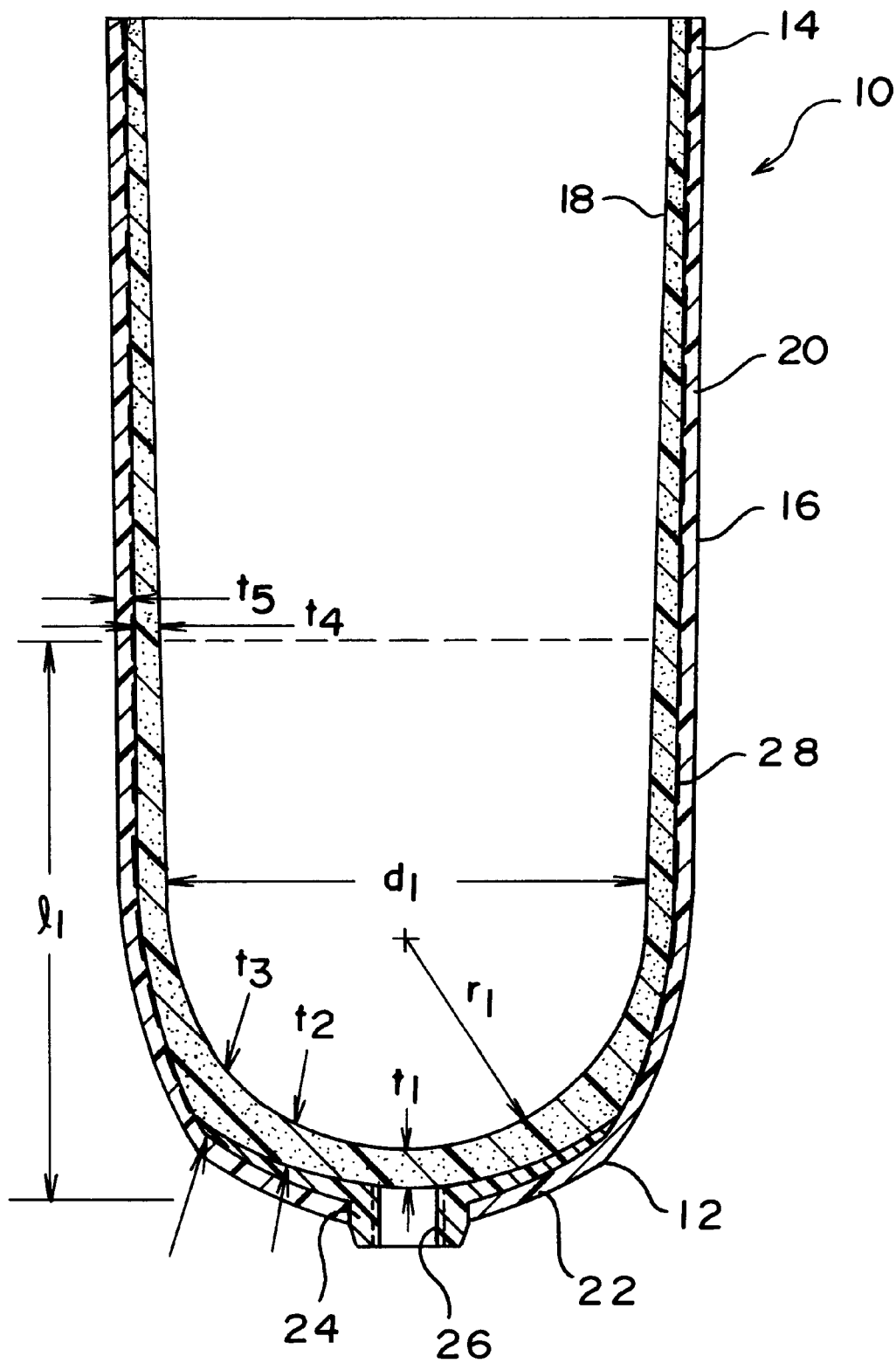

DUAL DUROMETER SILICONE LINER FOR PROSTHESIS

Priority of provisional application No. 60/045,704 filed May 6, 1997 is hereby claimed.

BACKGROUND OF THE INVENTION (a) Field of the Invention

This invention is in the field of suspension liners intended to be used with prosthetic devices.

(b) Related Technology

Prosthesis suspension liners formed from silicone elastomeric materials have been described in prior patents, such as, for example, U.S. Pat. No. 4,923,474 issued May 8, 1990 to Klasson and Kristinsson (an inventor named in this application); U.S. Pat. No. 5,507,834 granted Apr. 16, 1996 to Laghi; and U.S. Pat. No. 5,376,129 granted Dec. 27, 1994 to Falkner and Walsh. Elastomeric suspension liners are used to cushion a post-operative stump or residual limb with respect to a prosthesis that is installed over the residual limb and coupled to the sleeve by a locking element, for example as described in the Falkner and Walsh patent No. 5,376,129. The suspension of the prosthesis occurs due to the suction of the liner against the residual limb (giving rise to the term "suction socket" used for such liners).

It is highly desirable in such liners that they conform closely with the residual limb, accommodate all surface contours and sub-surface bone elements of the residual limb and provide a comfortable cushion between the residual limb and the hard socket of the prosthesis that is to be fitted over the residual limb.

Special silicone rubber or elastomer materials have been formulated as suitable substances for suspension liners. Such elastomer materials having suitable hardness (or softness), elongation, tensile and other properties (sterilizability, non-porous, easily cleanable, etc.) have been used successfully for suspension liners.

The liner member disclosed in the Kiasson and Kristinsson U.S. Pat. No. 4,923,474 includes an elasticity controlling matrix material at the distal end of the sleeve that does not impede elasticity of the elastomer radially within the normal range of radial distension of the liner in normal use, but renders the liner substantially inelastic axially during use to minimize the "pumping" effect that can occur with a fully resilient liner at the distal end of a residual limb that may not be fully healed or sealed as discussed in this patent.

However, it is highly desirable to increase the comfort of such sleeve liners to enhance their ability to conform to irregularities on the residual limb, to accommodate a wider variety of residual limbs with fewer sizes of liners; and to provide the amputee with a total feeling of comfort at the residual limb interface with the prosthesis, all while maintaining strength and durability of the liner.

BRIEF SUMMARY OF THE INVENTION

The invention comprises a silicone rubber suspension liner for a prosthesis wherein the liner is formed of a closed end, air tight inner layer of silicone rubber that is soft and highly compliant, and an outer layer having a hardness that is higher than that of the inner layer. In effect, the liner has a dual durometer or hardness, with the inner layer having a softer durometer than the outer layer. An elasticity controlling matrix layer may be provided within the silicone elastomer of the liner between the layers to provide anisotropy of elasticity between radial and axial directions, with the liner remaining radially elastic but substantially inelastic axially at the distal end area of the liner.

The liner preferably includes a relatively rigid interface "umbrella" element to which a prosthesis coupling or locking pin can be fastened at its distal end.

The composite, dual durometer liner preferably is formed using a simple, two-step molding process in which the firmer outer layer is cast and vulcanized over the inner, softer layer after the inner layer has been cast and vulcanized on a mandrel or male mold element.

BRIEF DESCRIPTION OF THE DRAWINGS

The drawing FIGURE illustrates a dual durometer silicone elastomer suspension liner for a prosthesis in accordance with the invention.

DETAILED DESCRIPTION

In the drawing, a silicone elastomer liner 10 intended for use between a residual limb and a prosthesis (not illustrated) includes a distal end 12, a proximal end 14 and an axially extending mid-portion 16 between the distal and proximal ends 12,14. The liner is air-tight when donned over a residual stump.

The entire liner 10 is formed of two layers of silicone elastomer to be described in more detail below, the inner layer 18 extending throughout the inner surface of the liner 10 and the outer layer 20 overlaying and contiguous with the outer surface of the inner layer 18, the interface between the layers 18 and 20 constituting a seamless, integral, permanent connection between the layers.

Preferably, at least the inner layer 18 tapers in thickness from a relatively thick cross-section at the distal end 12 of the liner to a thinner cross-section at the proximal end 14 of the liner. The outer layer 20 has a generally uniform thickness along the mid-portion 16 with a thickened distal end portion 22, although its outer configuration can be varied by a suitable outer mold cavity.

A relatively rigid prosthesis connecting "umbrella" element 24 having a concave curved configuration as shown and a threaded socket 26 for receiving a prosthesis locking pin (not illustrated) is provided at the distal end 12 of the liner 10, preferably embedded in the silicone elastomer between the inner and outer layers 18,20. The connecting element 24 is intimately bonded to the silicone elastomer constituting the liner 10.

An elasticity controlling matrix material 28 is provided between the layers 18,20 in the distal end area 12 of the liner 10, the matrix reinforcement material being relatively compliant in a radial direction and substantially rigid or inelastic in the axial direction. The matrix material 28 in the preferred embodiment extends over the distal or outer side of the prosthesis connecting element 24 using an assembly and molding process to be described below.

The liner 10 is fabricated in a sufficient number of sizes to accommodate various sizes of residual limbs. In use, a liner of the type described is rolled up from the proximal to the distal end, placed over the distal end of the residual stump and rolled back up or "donned" over the stump like a stocking. This procedure and the benefits achieved thereby are described in detail in the Klasson and Kristinsson U.S. Pat. No. 4,923,474.

Fabricating the sleeve liner is carried out as follows. For each specific liner size, three mold sections consisting of two outer mold sections and an inner mold section are provided. The first shot outer mold section is configured to give a specific thickness of the liner inner layer 18 while the second shot outer mold section is configured to provide a specific thickness of the outer layer 20 covering the inner layer 18, the matrix 28 and the connecting element 24. The inner mold section is a male form conforming to the inner surface of the liner. The outer mold sections are female molds that fit over the inner mold and provide a space between the inner and outer mold sections for receiving liquid silicone elastomer that is injected under pressure between the mold sections during the liner mold or casting process.

To form the inner layer 18, the inner mold is kept at a steady temperature slightly above ambient or room temperature (typically 35° C.) and the first shot outer mold is placed over the inner mold, centered and secured. Silicone material forming the inner layer is injected into the top of the outer mold section under a pressure of 40–100 psi and the mold is filled. The temperature is elevated to a desired level (70–125° C.) for curing or vulcanizing the first layer and then lowered after the silicone material has set.

The first shot outer mold section is then removed leaving the cured inner layer 18 of silicone elastomer exposed on the inner mold fixture. The correct size prosthesis connecting element 24 is placed on top of the inner layer (typically the inner mold element extends in an upright direction with the liner inverted) and an appropriate length of matrix material in the form of a woven tubular stockinette is placed over the connecting element and stretched over the outer surface over an appropriate length of the inner layer of silicone material.

The second shot outer mold section is then placed over the inner mold section, the inner layer of silicone elastomer, the connecting element and the matrix material, and is centered and secured. A small centering screw may be tightened through the injection port for the silicone material of the outer second shot mold section which extends into the threaded socket 26 of the connecting element 24 to center and secure the connecting element 24 while the second shot mold is being filled. Silicone elastomer used to form the outer layer 20 of the liner is then injected between the outer surface of the inner layer of silicone and the outer second shot mold to fill the mold. The temperature is elevated to the desired curing or vulcanizing temperature (70–125° C.) and lowered again after the material has set. The outer mold section is then removed, leaving the cured, dual layered liner exposed on the inner mold section with the contained connecting element and matrix material in the liner.

The second layer of silicone material bonds intimately with the inner layer during the second molding procedure so that the two layers are contiguous and joined together virtually seamlessly over the outer surface of the inner layer, with the matrix 28 material filled with silicone elastomer material constituting the outer layer 20 of the liner. The connecting element 24 is intimately bonded between the two layers as well so that the entire structure of the liner is integrally connected together.

The molded liner is then removed from the inner mold section and prepared for packing and shipment.

The silicone elastomer used to form the inner layer 18 comprises a vinyl terminated polydimethylsiloxane (vinyldimethylsiloxy terminated dimethylpolysiloxane) cured or vulcanized by reaction with a suitable crosslinker. The silicone elastomer is reinforced with silica (preferably fumed silica having a surface area of 200 m$^2$/g.) and this increases the strength of the cured or crosslinked silicone. The degree of crosslinking can be adjusted to some extent by adjusting the concentration of crosslinker. The component in the elastomer that the crosslinker reacts with is typically a vinyl group that is on the ends of the polysiloxane. The end groups on the polysiloxane also control the viscosity of the silicone and the concentration can be varied to allow a formulator to manufacture polysiloxanes of various viscosities. Specifically, more than one end blocking moiety is used to provide control of viscosity and level of crosslinking somewhat independently of each other. The preferred viscosity is in the range of 90,000–100,000 cPs. Non-functional endblocking (trimethyl siloxy) is used in conjunction with vinyl endblocking (vinyldimethyl siloxy) to allow the production of a polysiloxane with a lower vinyl concentration than would otherwise be necessary if vinyl endblocking was used exclusively. This technique permits the production of low viscosity silicones having a somewhat lower density crosslinking than is commonly used in silicone elastomers. The organopolysiloxane contains silyl groups of the formula $R_1R_2$—SiO and end blockers of the formula $R_3R_4R_5$—SiO$_{0.5}$, $R_1$ and $R_2$ groups independently are lower alkyl of 1 to 6 carbons, phenyl or trifluoropropyl. Preferably the $R_1$ and $R_2$ groups are both methyl. Therefore, in the preferred embodiment of the composition the $R_1R_2$—SiO group represents dimethylsiloxane. $R_3$, $R_4$ and $R_5$ groups independently are lower alkyl of 1 to 6 carbons, phenyl, vinyl, allyl or other olefinic group having up to 4 carbons. In the preferred embodiment, $R_4$ and $R_5$ are methyl and $R_3$ is vinyl or methyl. Optionally, the molar concentration of vinyl in $R_3$ may be varied from as high as 100% vinyl to as low as 30% vinyl, the remaining fraction being methyl. Preferentially, $R_3$ is vinyl at 80% and methyl at 20% concentration.

The composition contains trimethyl silyl treated silica as a reinforcer in the weight ratio of approximately 12 to 45 parts of reinforcer to 100 parts of polymer. The preferred invention contains 17 parts of silica to 100 parts of polymer. The silica must be treated with a reagent to neutralize the active sites on its surface, usually using hexamethyldisilazane.

Organopolysiloxane of lower viscosity, 100 to 10,000 cP is added to the composition to reduce viscosity, modulus and tensile set. The quantity of organopolysiloxane can be adjusted to give the desired property profile. The preferred organopolysiloxane is trimethyl siloxy terminated dimethylpolysiloxane with viscosity of 1000 cP.

The elastomer is made in two components, called part "A" and "B". Part A is constituted of the polydimethylsiloxane that is vinyl and methyl terminated. A platinum catalyst is used, the catalyst comprising a complex of platinum with vinyl-containing oligosiloxanes (complex of platinum and divinyltetratramethyldisiloxane with typical levels of active platinum of 5 to 50 parts per million.

Part B of the two components of the elastomer includes a polydimethylsiloxane and silica identical to that in part A. This part B also includes a polydimethylsiloxane with hydrogen on the chain commonly called methyl hydrogen which acts as a crosslinker. With the sum of the mass of polydimethylsiloxane and silica constituting 100 parts, crosslinker concentration can vary from as low as 0.3 to as high as 4 parts per hundred parts. A crosslinking inhibitor is included in part B that comprises an oligosiloxane with high concentration of vinyl-containing substituents of any of the class of compounds known as acetylinic alcohols. The preferred inhibitor is tetravinyl tetramethyl cyclotetrasiloxane. The inhibitor may be used in concentrations as low as 0.02 parts per hundred parts to as high as 0.5 parts per hundred parts.

In forming the inner layer, parts A and B are mixed together before injection in the mold in a 1:1 ratio by weight.

The silicone elastomer just described above is obtainable from NuSil Technology of Carpinteria, Calif., under product designation CF13-2188.

The preferred outer layer 20 of the liner 10 is constituted of a vinyl terminated polydimethylsiloxane cured or vulcanized by reaction with a suitable crosslinker. The silicone is typically reinforced with silica, the degree of crosslinking being controlled by the concentration of crosslinker. This silicone material is also obtainable from NuSil Technology of Carpinteria, California, under product designation CF3-2188-1. The silicone elastomer is addition-cured using a platinum catalyst of the type described above in connection with the NuSil product CF13-2188 silicone elastomer. The silicone elastomer used in the outer layer also is provided as two components, parts "A" and "B".

Part A is made from polydimethylsiloxane that is vinyl terminated and a second polydimethylsiloxane that is trimethyl terminated. Trimethyl terminated polymer is included at a concentration of 1–10% and silica is included in the formulation for reinforcement. The viscosity of the uncured part A elastomer used to form the outer layer of the liner is 250,000–800,000 cPs. The silica is treated with a reagent to neutralize the active sites on its surface using, preferably, hexamethyldisilazane, with the concentration of silica being in the range of 12–45 parts per hundred parts of polysiloxane, with a preferred concentration being 25 parts per hundred per one hundred parts of polysiloxane. Titanium dioxide is added to the part A component of the silicone elastomer in concentration sufficient to color it opaque white in a concentration of 2–15%, if a white color is desired. A platinum catalyst is added to the part A component, the catalyst comprising a complex of platinum and divinyltetramethyldisiloxane with a level of active platinum typically from 5–50 parts per million.

The part B component of the CF3-2188 silicone elastomer comprises polydimethylsiloxane and silica identical to that used in part A described above and a crosslinker. Typically, part B contains no pigment, and is translucent. Assuming the sum of the mass of polydimethylsiloxane and silica to constitute 100 parts, polydimethylsiloxane with hydrogen on the chain (commonly called methyl hydrogen) is used as the crosslinker in concentrations extending from 0.3 to 4.0 parts per hundred. A crosslinking inhibitor is added to part B in the form of an oligosiloxane with a high concentration of vinyl-containing substituents or any of the class of compounds known as acetylinic alcohols to control rate of crosslinking. The preferred inhibitor is tetravinyl tetramethyl cyclotetrasiloxane in concentrations from about 0.02 parts per hundred to 0.5 parts per hundred.

When forming the outer layer 20, parts A and B of the NuSil CF3-2188-1 silicone elastomer are mixed in a ratio of 1:1 to cause crosslinking by hydrosilylation, with the inhibitor allowing control of the rate of crosslinking of the two parts when they are mixed together.

When the inner and outer layers are formed using the silicone elastomers described above, the following physical characteristics of the layers are obtained:

| Characteristic | Inner Layer | Outer Layer |
| --- | --- | --- |
| Transparency | Translucent | Translucent |
| Shore A | Not Measurable | 6 |
| Shore 00 | 32–45 | 52 |
| Tensile Strength (min) (p/in) | 233 | 350 |

-continued

| Characteristic | Inner Layer | Outer Layer |
| --- | --- | --- |
| Tensile Strength (max) (p/in) | 500 | 551 |
| Elongation (%) | 1000 | 1150 |
| Modulus 100% (psi) | 8 | 21 |
| Modulus 200% | 26 | 53 |
| Modulus 500% | 61 | 139 |
| Tear Strength (nick) (p/in) | 49 (0.002") | 84 (0.005") |

The elasticity controlling matrix material 28 is obtainable from OTTO BOCK ORTHOPEDIC INDUSTRY, INC. of Minneapolis, Minn. under Product Number 623T10 in 12 cm and 15 cm lengths, this material being a white woven polyamide stockinette. The matrix material is fully compliant and stretchable in the radial direction within the range of normal liner distension but is substantially inelastic or non-stretchable in the longitudinal direction when installed in the liner.

It will be seen from the shore hardness properties of the inner and outer layers 18, 20 that the inner layer is considerably softer than the outer layer, and has a lower tear strength than the outer layer. The outer layer possesses greater hardness and tear strength, which serves to reinforce the softer inner layer and provides a product that is both strong and durable, while very comfortable for the user. The ability of the inner layer 18 to conform to the skin surface of the residual limb of the user reduces any gaps between the skin and the inner layer which tends to reduce perspiration between the residual limb and the inner surface of the liner, a characteristic that is highly desirable in a liner of this type.

Friction properties of the inner, softer liner against the skin of the residual limb are such that a higher shear force is needed to cause slippage between the inner layer and the skin as compared with prior art silicone elastomer liners, which enhances the suspension properties and comfort of the liner.

The viscosity of the liquid silicone elastomer used to form both layers 18 and 20 is low enough to allow rapid injection molding of large parts. The preferred viscosities are in the range of 90,000 to 100,000 cPs. The formulation of the outer layer 20 may be varied, provided that the physical property characteristics of the outer layer as described above remain essentially consistent, particularly with regard to a Shore 00 hardness which must be higher than that the inner layer 18. Typically, the tensile and tear strengths of the outer layer will be higher than these strengths of the inner layer. It is also preferred that the outer layer have a higher elongation and modulus than the inner layer.

Coloration of the liner is optional, and one example has been described above wherein the inner layer is colored white and the outer layer is translucent.

Typical preferred dimensions of exemplary liners constructed in accordance with the invention are shown below, with reference to the drawing that indicates the locations where the measurements are taken

|  | Small | Large |
| --- | --- | --- |
| $t_1$ (mm) | 6 | 9 |
| $t_2$ (mm) | 5 | 4.5 |
| $t_3$ (mm) | 6.5 | — |

-continued

|  | Small | Large |
|---|---|---|
| $t_4$ (mm) | 2.7 | 1.7 |
| $t_5$ (mm) | 2.4 | 2.2 |
| $r_1$ (cm) | 40 | 70 |
| $l_1$ (cm) | 8–9 | 13–14 |
| $l_t$ (cm) | 34 | 40 |
| $d_1$ (cm) | 9 | 28.6 |
| W (gm) | 230 | 880 | where the measurements are described as follows:

$t_1$—inner layer thickness
$t_2$—inner layer thickness
$t_3$—inner layer thickness
$t_4$—inner layer thickness
$t_5$—outer layer thickness
$r_1$—radius of liner end
$l_1$—length of matrix
$l_t$—total length of liner
$d_1$—inside diameter
W—weight of liner An exemplary embodiment of the invention has been described and it is to be understood that persons skilled in the art may change structural details of the preferred embodiment without departing from the scope of the invention, which is to be limited solely by the scope and meaning of the appended claims.

What is claimed is:

1. A residual limb suspension liner for a prosthesis comprising:
    a closed-ended, air-tight tubular sleeve adapted to envelop the distal end area of a residual limb;
    said sleeve formed over its entire length of inner and outer layers of different silicone elastomers, said layers being contiguous and integrally joined to each other along the entire outer surface of the inner layer;
    the silicone elastomer of said inner layer having a Shore A hardness that is below Shore A practical measurement, and the silicone elastomer of said outer layer having Shore A hardness of approximately 6.

2. The residual limb suspension liner as claimed in claim 1, wherein the inner and outer layers have the following additional characteristics:

| Characteristic | Inner Layer | Outer Layer |
|---|---|---|
| Tensile Strength (min.) (p/in) | 233 | 350 |
| Modulus 100% (psi) | 8 | 21 |
| Modulus 200% | 26 | 53 |
| Modulus 500% | 61 | 139 |
| Tear Strength (nick) (p/in) | 49 (0.002") | 84 (0.005"). |

3. The residual limb suspension liner as claimed in claim 2, including an elasticity controlling matrix at least in a distal end area of said liner, said matrix causing said distal end area to be substantially inelastic in the axial direction without interfering with radial elasticity of the silicone elastomers within a range of distension of the liner during normal use.

4. The residual limb suspension liner as claimed in claim 3, wherein the matrix is filled with silicone elastomer and covers at least a portion of the inner layer between the inner and outer layers so as to constitute the outer surface of the inner layer over such portion.

5. The residual limb suspension liner as claimed in claim 4 wherein the inner and outer layers are translucent.

6. The residual limb suspension liner as claimed in claim 4 wherein the inner layer is white in color and the outer layer is translucent.

7. The residual limb suspension liner as claimed in claim 4, including a prosthesis connector at the distal end of the liner.

8. The residual limb suspension liner as claimed in claim 2, wherein the inner and outer layers have the following additional characteristics:

|  | Inner Layer | Outer Layer |
|---|---|---|
| Tensile Strength (max.) (p/in) | 500 | 551 |
| Elongation (%) | 1000 | 1150. |

9. The residual limb liner as claimed in claim 2, wherein the inner and outer layers are translucent.

10. The residual limb suspension liner as claimed in claim 2 wherein the inner layer is white in color and the outer layer is translucent.

11. A residual limb suspension liner for a prosthesis comprising:
    a closed-ended, air-tight tubular sleeve adapted to envelop the distal end area of a residual limb;
    said sleeve formed over its entire length of inner and outer layers of different silicone elastomers, said layers being contiguous and integrally joined to each other along the outer surface of the inner layer;
    the silicone elastomer of said inner layer having a lower hardness than the hardness of the silicone elastomer of said outer layer; and
    an elasticity controlling matrix at least in a distal end area of said liner, said matrix causing said distal end area to be substantially inelastic in the axial direction without interfering with radial elasticity of the silicone elastomers within a range of distension of the liner during normal use.

12. The residual limb suspension liner as claimed in claim 11, wherein the matrix is filled with silicone elastomer and covers at least a portion of the inner layer between the inner and outer layers so as to constitute the outer surface of the inner layer over such portion.

13. The residual limb suspension liner as claimed in claim 12 wherein the inner and outer layers are translucent.

14. The residual limb suspension liner as claimed in claim 12, wherein the inner layer is white in color and the outer layer is translucent.

15. The residual limb suspension liner as claimed in claim 12, including a prosthesis connector at the distal end of the liner.

16. The residual limb suspension liner as claimed in claim 11, wherein the inner and outer layers have the following additional characteristics:

|  | Inner Layer | Outer Layer |
|---|---|---|
| Tensile Strength (max.) (p/in) | 500 | 551 |
| Elongation (%) | 1000 | 1150. |

17. The residual limb liner as claimed in claim 11, wherein the inner and outer layers are translucent.

18. The residual limb suspension liner as claimed in claim 11, wherein the inner layer is white in color and the outer layer is translucent.

19. A residual limb suspension liner for a prosthesis comprising:

a closed-ended, air-tight tubular sleeve adapted to envelop the distal end area of a residual limb;

said sleeve formed over its entire length of inner and outer layers of different silicone elastomers, said layers being contiguous and integrally joined to each other along the outer surface of the inner layer;

the silicone elastomer of said inner layer having a lower hardness than the hardness of the silicone elastomer of said outer layer;

said inner and outer layers have the following characteristics:

| Characteristic | Inner Layer | Outer Layer |
| --- | --- | --- |
| Tensile Strength (min.) (p/in) | 233 | 350 |
| Modulus 100% (psi) | 8 | 21 |
| Modulus 200% | 26 | 53 |
| Modulus 500% | 61 | 139 |
| Tear Strength (nick) (p/in) | 49 (0.002") | 84 (0.005"). |

20. The residual limb suspension liner as claimed in claim 19, including an elasticity controlling matrix at least in a distal end area of said liner, said matrix causing said distal end area to be substantially inelastic in the axial direction without interfering with radial elasticity of the silicone elastomer within a range of distension of the liner during normal use.

21. The residual limb suspension liner as claimed in claim 20, wherein the matrix is filled with silicone elastomer and covers at least a portion of the inner layer between the inner and outer layers so as to constitute the outer surface of the inner layer over such portion.

* * * * *